United States Patent
Lin et al.

(10) Patent No.: US 10,441,208 B2
(45) Date of Patent: Oct. 15, 2019

(54) MUSCLE POWER DETECTION DEVICE AND METHOD FOR MUSCLE POWER CLASSIFICATION

(71) Applicants: METAL INDUSTRIES RESEARCH & DEVELOPMENT CENTRE, Kaohsiung (TW); Kaohsiung Veterans General Hospital, Kaohsiung (TW)

(72) Inventors: Hsuan-Chih Lin, Kaohsiung (TW); Ming-Hui Cheng, Kaohsiung (TW); Tzyy-Ker Sue, Kaohsiung (TW); Chiu-Feng Lin, Pingtung County (TW); Ko-Long Lin, Kaohsiung (TW)

(73) Assignees: METAL INDUSTRIES RESEARCH & DEVELOPMENT CENTRE, Kaohsiung (TW); Kaohsiung Veterans General Hospital, Kaohsiung (TW)

( * ) Notice: Subject to any disclaimer, the term of this patent is extended or adjusted under 35 U.S.C. 154(b) by 394 days.

(21) Appl. No.: 15/393,278

(22) Filed: Dec. 29, 2016

(65) Prior Publication Data
US 2018/0140244 A1   May 24, 2018

(30) Foreign Application Priority Data
Nov. 24, 2016  (TW) .............................. 105138678 A

(51) Int. Cl.
*A61B 5/00* (2006.01)
*A61B 5/22* (2006.01)
*A61B 5/11* (2006.01)

(52) U.S. Cl.
CPC ............ *A61B 5/224* (2013.01); *A61B 5/0053* (2013.01); *A61B 5/1121* (2013.01);
(Continued)

(58) Field of Classification Search
CPC ... A61B 5/0053; A61B 5/1121; A61B 5/1124; A61B 5/1126; A61B 5/6824
See application file for complete search history.

(56) References Cited

U.S. PATENT DOCUMENTS

| 6,792,801 B2 | 9/2004 | Hoggan et al. |
| 7,661,309 B2 | 2/2010 | Lan et al. |

(Continued)

FOREIGN PATENT DOCUMENTS

| TW | M397238 U1 | 2/2011 |
| TW | 201311214 A | 3/2013 |

(Continued)

*Primary Examiner* — Max F Hindenburg
(74) *Attorney, Agent, or Firm* — CKC & Partners Co., LLC

(57) ABSTRACT

A muscle power detection device and a muscle power detection method for detecting and classifying a muscle power status of a subject are provided. The muscle power detection device includes an inertia measurement unit, a pressure detection unit and a processing unit. The inertia measurement unit is configured to be arranged at a part of the subject and to obtain inertial data corresponding to the part of the subject according to movement status of the part of the subject. The pressure detection unit is configured to detection external force applied on the part of the subject to obtain pressure data. The processing unit is configured to perform an operation on the inertial data and the pressure data for obtaining evaluation values, and to obtain muscle power information corresponding to the part of the subject according to the evaluation values.

7 Claims, 8 Drawing Sheets

(52) U.S. Cl.
CPC .......... *A61B 5/6824* (2013.01); *A61B 5/7264* (2013.01); *A61B 2505/09* (2013.01); *A61B 2562/0219* (2013.01); *A61B 2562/0247* (2013.01)

(56) References Cited

U.S. PATENT DOCUMENTS

| | | | |
|---|---|---|---|
| 9,005,141 B1* | 4/2015 | Najafi | A61B 5/1116 600/595 |
| 9,706,950 B2* | 7/2017 | Glaser | A61B 5/1116 |
| 9,804,189 B2* | 10/2017 | Takenaka | G01P 15/18 |
| 10,123,751 B2* | 11/2018 | Petterson | A61B 5/0022 |
| 10,188,322 B2* | 1/2019 | Piijl | G06K 9/00342 |

FOREIGN PATENT DOCUMENTS

| | | |
|---|---|---|
| TW | I455705 B | 10/2014 |
| TW | M537471 U | 3/2017 |

* cited by examiner

MUSCLE POWER DETECTION DEVICE AND METHOD FOR MUSCLE POWER CLASSIFICATION

RELATED APPLICATIONS

This application claims priority to Taiwanese Application Serial Number 105138678, filed on Nov. 24, 2016, which is herein incorporated by reference.

BACKGROUND

Field of the Invention

The invention relates to a device and a method for detecting a muscle power status of a subject, and more particularly to a device and a method for determining corresponding muscle power grade information according to a movement status of a subject.

Description of Related Art

With the development of medical technologies and the improvement of environmental health, the average life expectancy in the world has been prolonged in recent decades. However, the number of patients suffering brain and nervous diseases also increases with changes of eating habits and increase of living stress. If the central nervous system is damaged, a sequela such as limb hemiplegia would be induced, and thus the body cannot freely move. Consequently, health cares to the limb hemiplegia caused by brain or nerve damage and medical issues need to be concerned. On the other hand, more and more traffic and sports injuries happen as traffic and sports activities become more frequent. If a tissue (e.g. a nerve or a muscle) is damaged, the damaged part of the patient would not move normally. For a patient who has a body movement problem, the quality of rehabilitation treatment would affect the recovery effect and speed. In general, if a patient's health status can be accurately evaluated and a suitable treatment can be provided, the patients recovery status can be improved, and the rehabilitation duration of the patient can be effectively reduced.

For current rehabilitation treatments, an evaluation of a patient's muscle power is performed according to the experience of a medical staff, such as a doctor, a physiotherapist and a physical therapist. However, a risk of misdiagnosis of a patient's muscle power by a subjective determination would occur, which results in an erroneous treatment. On the other hand, although the instruments for muscle tone testing have been developed in the industry, many medical units have little interest in adopting the conventional muscle power evaluation instruments due to their expensive prices and huge sizes.

SUMMARY

An objective of the invention is to provide a muscle power detection device and a method for muscle power classification which can obtain muscle power grade information of a subject according to angle data and velocity data, so as to evaluate a muscle movement status of the subject.

One aspect of the invention is directed to a muscle power detection device configured to detect muscle power of a subject. The muscle power detection device includes an inertia measurement unit, a pressure detection unit and a processing unit. The inertia measurement unit is configured to be arranged at a part of the subject and to obtain inertial data corresponding to the part of the subject according to a movement status of the part of the subject. The pressure detection unit is configured to detect external force applied on the part of the subject to obtain pressure data. The processing unit is configured to perform an operation on the inertial data and the pressure data for obtaining an evaluation value and to obtain muscle power grading information corresponding to the part of the subject according to the evaluation value. The evaluation value includes an angle, a speed, an angle variation, a speed variation, or combinations thereof.

In accordance with some embodiments of the invention, the inertial data of the part of the subject obtained from the inertia measurement unit include angle data and acceleration data. The angle data and the acceleration data are used to be converted by the processing unit to the evaluation value.

In accordance with some embodiments of the invention, the inertia measurement unit includes at least one of a gyroscope, an accelerometer and an orientation sensor.

In accordance with some embodiments of the invention, the muscle power grading information includes Medical Research Council (MRC) muscle power grade information.

In accordance with some embodiments of the invention, the muscle power detection device further includes a notification unit configured to indicate the muscle power grading information.

Another aspect of the invention is directed to a muscle power detection device configured to detect muscle power of a subject. The muscle power detection device includes a first inertia measurement unit, a second inertia measurement unit, a pressure detection unit and a processing unit. The first inertia measurement unit is configured to be arranged at a first part of the subject and to obtain first inertial data corresponding to the first part of the subject according to a movement status of the first part of the subject. The second inertia measurement unit is configured to be arranged at a second part of the subject and to obtain second inertial data corresponding to the second part of the subject according to a movement status of the second part of the subject. The first part of the subject and the second part of the subject are substantially different. The pressure detection unit is configured to detect external force applied on the first part of the subject or the second part of the subject to obtain pressure data. The processing unit is configured to perform an operation on the first inertial data, the second inertial data and the pressure data for obtaining an evaluation value and to obtain muscle power grading information corresponding to the first part of the subject and the second part of the subject according to the evaluation value. The evaluation value includes an angle, a speed, an angle variation, a speed variation, or combinations thereof.

In accordance with some embodiments of the invention, at least one of the first inertial data of the first part of the subject obtained from the first inertia measurement unit and the second inertial data of the second part of the subject obtained from the second inertia measurement unit include angle data and acceleration data. The angle data and the acceleration data are used to be converted by the processing unit to the evaluation value.

In accordance with some embodiments of the invention, the muscle power grading information includes MRC muscle power grade information.

Another aspect of the invention is directed to a muscle power detection method for detecting muscle power of a subject. The muscle power detection method includes: arranging at least one inertia measurement unit at parts of the subject to obtain inertial data corresponding to the parts of the subject according to a movement status of the parts of the subject; arranging a pressure detection unit on one of the parts of the subject to detect external force applied on the part of the subject to obtain pressure data; and performing an operation on the inertial data and the pressure data to obtain an evaluation value and to obtain muscle power grading information corresponding to the parts of the subject according to the evaluation value. The evaluation value includes an angle, a speed, an angle variation, a speed variation, or combinations thereof.

In accordance with some embodiments of the invention, the muscle power grading information includes MRC muscle power grade information.

BRIEF DESCRIPTION OF THE DRAWINGS

The foregoing aspects and many of the accompanying advantages of this invention will become more readily appreciated as the same becomes better understood by reference to the following detailed description, when taken in conjunction with the accompanying drawings.

DETAILED DESCRIPTION

The detailed explanation of the invention is described as following. The described preferred embodiments are presented for purposes of illustrations and description, and they are not intended to limit the scope of the invention.

It will be understood that, although the terms "first" and "second" may be used herein to describe various elements, components, stages, and/or signals, these elements, components, stages, and/or signals should not be limited by these terms. These terms are only used to distinguish elements, components, stages, and/or signals.

In the following description and claims, the term "coupled" along with their derivatives, may be used. In particular embodiments, "coupled" may be used to indicate that two or more elements are in direct physical or electrical contact with each other, or may also mean that two or more elements may not be in direct contact with each other. "Coupled" may still be used to indicate that two or more elements cooperate or interact with each other.

Figure 1A:
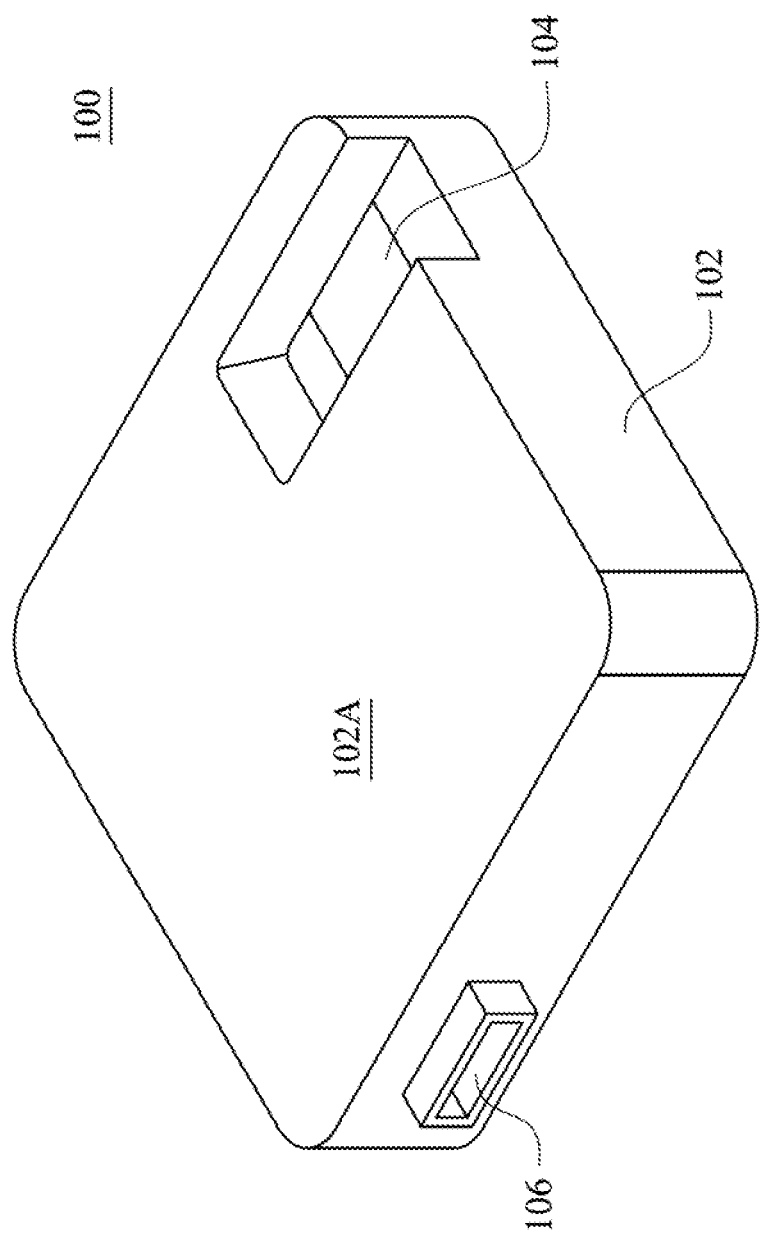
FIG. 1A is a schematic external view of a muscle power detection device in accordance with some embodiments of the invention.
Figure 1B:
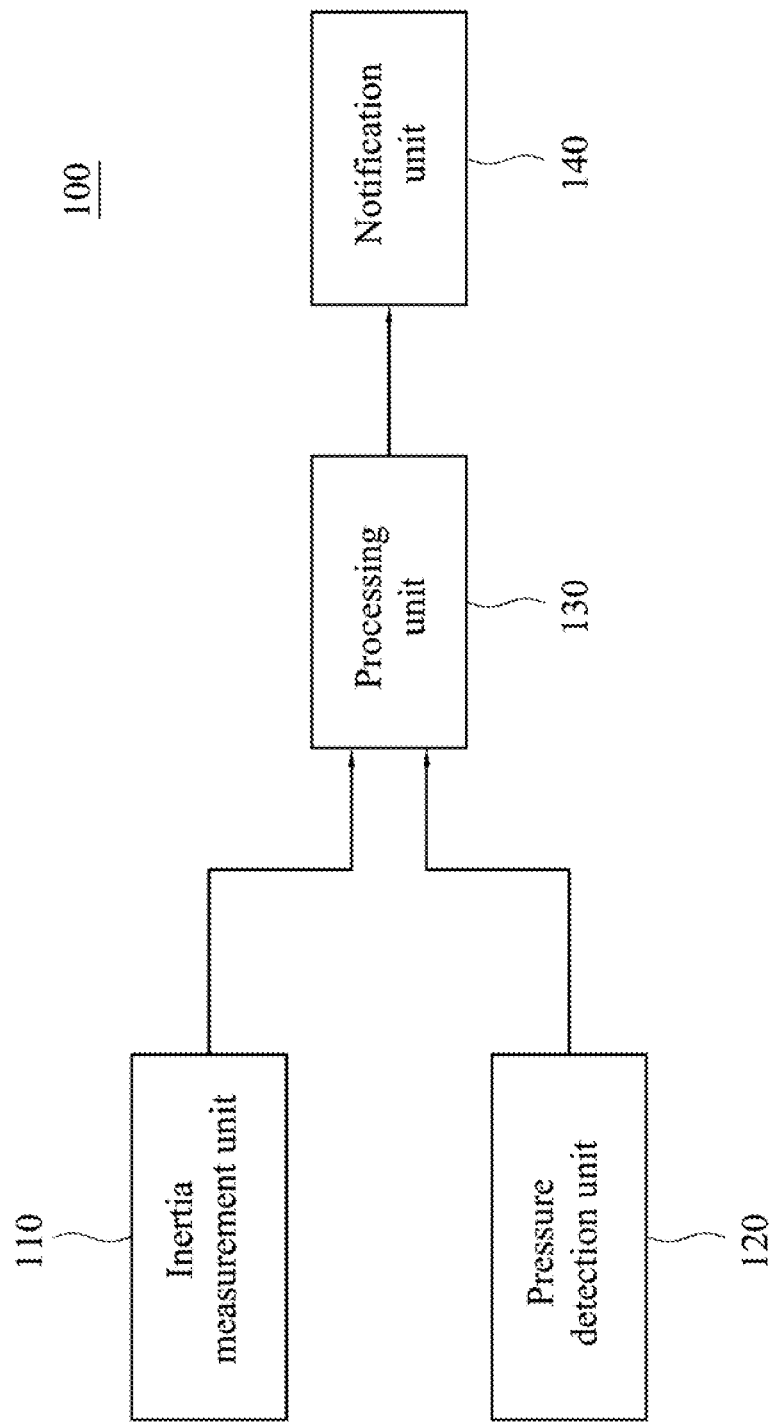
FIG. 1B is a functional block diagram of the muscle power detection device shown in FIG. 1A.

Referring to FIG. 1A and FIG. 1B, FIG. 1A is a schematic external view of a muscle power detection device 100 in accordance with some embodiments of the invention, and FIG. 1B is a functional block diagram of the muscle power detection device 100 in accordance with some embodiments of the invention.

The muscle power detection device 100 is configured to detect a muscle power status of a subject and to evaluate a muscle and joint movement status according to the muscle power status. The appearance of the muscle power detection device 100 is mainly a housing 102 of which the interior includes an inertia measurement unit 110, a pressure detection unit 120, a processing unit 130 and a notification unit 140. The housing 102 is mainly for protecting the inertia measurement unit 110, the pressure detection unit 120, the processing unit 130, the notification unit 140 and other components therein. Furthermore, the housing 102 may further adopt a waterproof design, a shockproof design, a dropproof design and/or a dustproof design. The muscle power detection device 100 may be arranged at a part of the subject (e.g. a portion near the elbow joint, the knee joint, the wrist joint or the ankle joint) by a retaining ring, a zip, a hook and loop fastening structure, an elastic band or another component, but is not limited thereto.

The inertia measurement unit 110 is configured to obtain inertial data corresponding to the part of the subject according to the movement status of the part at which the muscle power detection device 100 is arranged. The inertia measurement unit 110 may be a nine-axis acceleration sensing module which includes a gyroscope, an accelerometer, an orientation sensor and/or another similar component, and the obtained inertial data thereof include three-axis data such as angular velocity data and acceleration data.

The pressure detection unit 120 is configured to detect the external force exerted on the muscle power detection device 100 which is arranged at the part of the subject, in order to obtain pressure data corresponding to the part. As shown in FIG. 1A, the housing 102 includes a force receiving surface 102A. The force receiving surface 102A is configured to accept an external force exerted from outside, and then the pressure detection unit 120 detects the external force applied on the force receiving surface 102A and converts the detecting result into pressure data. As a result, in the embodiments of the invention, a resistance may be provided to the subject by applying an external force to the pressure detection unit 120 as one of the conditions for the following muscle power grade determination.

The processing unit 130 is configured to perform sampling and operation on the inertial data obtained by the inertia measurement unit 110 in a predetermined testing time to obtain an evaluation value and to obtain the muscle power information corresponding to the part of the subject at which the muscle power detection device 100 is arranged according to the evaluation value. The evaluation value may include a combination selected from an angle, a velocity, an angle variation and/or a velocity variation. For example, the processing unit 130 performs operation on the angular velocity data and the acceleration data to obtain angle data and velocity data, and then obtain muscle power information according to the angle data and the velocity data. The testing time of the muscle power detection device 100 and the sampling rate of the processing unit 130 to the inertial data may be adjusted in accordance with, for example, the muscle characteristics (e.g. body height or sex) and the age of the subject.

In some embodiments, the processing unit 130 may further be configured to perform an operation on the pressure data obtained by the pressure detection unit 120 and to obtain the corresponding muscle power information according to the angle data and the velocity data in a pressure status.

In particular, the processing unit 130 may convert the pressure data, the angle data and the velocity data into a Medical Research Council (MRC) muscle power grade according to the MRC muscle scale. That is, the muscle power information obtained through the operation performed by the processing unit 130 may include an MRC muscle power grade. The MRC muscle scale includes 6 levels, in which the corresponding muscle movement descriptions are listed in TABLE 1.

TABLE 1

| MRC muscle power grade | Muscle movement description |
| --- | --- |
| 0 | No muscle contraction |
| 1 | Only slight muscle contraction, but no joint movement |
| 2 | Can move in a horizontal plane, but cannot move against the resistance of gravity |
| 3 | Can move against the resistance of gravity, but cannot move against an external force |
| 4 | Can move against the resistance of gravity and a part of external force |
| 5 | Can move normally |

The notification unit 140 may indicate the angle data, the velocity data, the pressure data, the testing time, the muscle power information, the stability information and/or another data or information obtained by the muscle power detection device 100 in various ways. For example, the notification unit 140 may transmit the pressure data, the testing time, the muscle power information (e.g. the MRC muscle power grade) and/or the stability information to the display unit 104 for real-time display. In some embodiments, the notification unit 140 may also show the muscle power information and/or the stability information in a form of sound or light signal.

In addition, in some embodiments, the processing unit 130 may further transmit the angular velocity data, the acceleration data, the angle data, the velocity data, the pressure data, the testing time and/or the stability information to a remote terminal (e.g. a computer or a smartphone) by any wired or wireless communication method.

Figure 2:
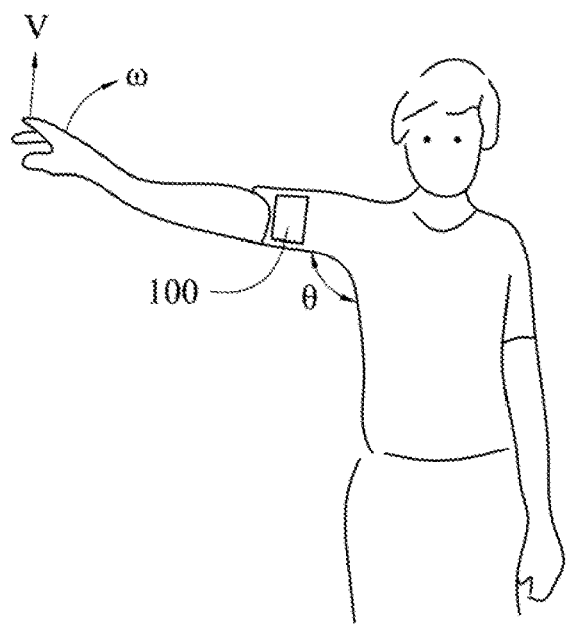
FIG. 2 exemplarily illustrates the muscle power detection device in accordance with some embodiments of the invention arranged on a subject to perform muscle power detection.

FIG. 2 exemplarily illustrates the muscle power detection device 100 arranged on a subject to perform muscle power detection. As shown in FIG. 2, the muscle power detection device 100 is arranged at the right arm of the subject, in which an angular velocity ω and an acceleration a are obtained by the inertia measurement unit 110 and then an angle θ and a velocity V are obtained by the operation of the processing unit 130, so as to obtain muscle power information of the right arm. If the operation result indicates that the angle θ is less than an angular threshold (which may be set between 0 and 5 degrees) and that the velocity V is close to 0, the processing unit 130 determines that there is no muscle contraction at the testing part; that is, the obtained MRC muscle power grade is 0. If the operation result indicates that the angle θ is greater than the angular threshold but less than about 90 degrees, the processing unit 130 determines that there is only slight muscle contraction but no joint movement at the testing part; that is, the obtained MRC muscle power grade is 1. If the operation result indicates that the angle θ is about but does not substantially exceed 90 degrees, the processing unit 130 determines that the testing part can move in a horizontal plane but cannot move against the resistance of gravity; that is, the obtained MRC muscle power grade is 2. If the operation result indicates that the angle θ substantially exceeds 90 degrees, an external force is further needed to be applied on the testing part, in order to further determine the obtained MRC muscle power grade from 3-5.

Figure 3:
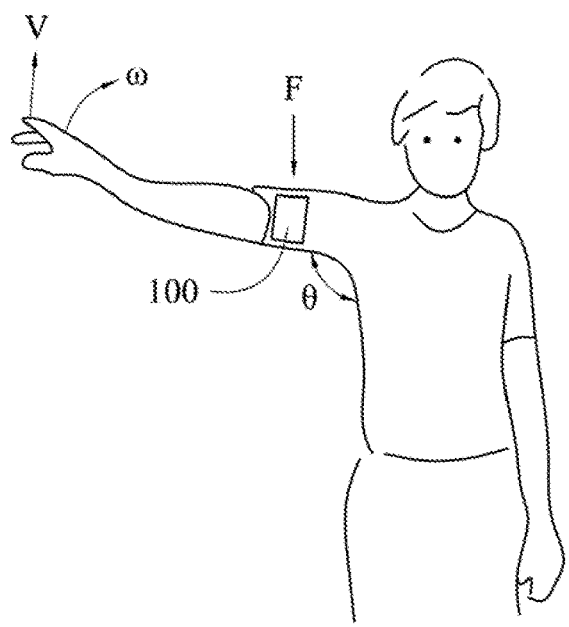
FIG. 3 exemplarily illustrates the muscle power detection device in accordance with some embodiments of the invention arranged on a subject to perform muscle power detection and to apply an external force on the muscle power detection device.

Next, referring to FIG. 3, when applying an external force F on the muscle power detection device 100, if the operation result indicates that the velocity V is greater than a velocity threshold and a variation quantity of the angle θ is greater than an angular variation threshold (the velocity threshold and the angular variation threshold are both greater than 0), the processing unit 130 determines that the testing part can move against the resistance of gravity but cannot move against an external force; that is, the obtained MRC muscle power grade is 3. If the operation result indicates that the velocity V is between 0 and the velocity threshold and the variation of the angle θ is between 0 and the angular variation threshold, the processing unit 130 determines that the testing part can move against the resistance of gravity and a part of external force; that is, the obtained MRC muscle power grade is 4. If the operation result indicates that the velocity V is substantially 0 and the variation of the angle θ is substantially 0, the processing unit 130 determines that the testing part can move normally; that is, the obtained MRC muscle power grade is 5. The external force F may be displayed by the display unit 104, in order to indicate the user whether the external force F applied on the muscle power detection device 100 is suitable. Similarly, the velocity threshold and the angular variation threshold may also be adjusted in accordance with, for example, the muscle characteristics and the age of the subject.

Furthermore, the processing unit 130 may further obtain the stability of the right arm according to the degree of variation of the angle θ and the velocity V. For example, if the variation quantity of the angle θ and the velocity V are too large or the variation counts thereof are too high, the processing unit 130 determines that the stability of the muscles of the right arm is insufficient; if the variation quantity and the variation count of the angle θ and the velocity V are in satisfied ranges (the satisfied ranges may be adjusted in accordance with practical operations), the processing unit 130 determines that the muscles of the right arm have good stability.

The muscle power detection device 100 may further include an interface 106 for connecting a power transmission line and/or a signal transmission line. For example, a power source may transmit power to the muscle power detection device 100 for operation via the interface 106. In some embodiments, if the muscle power detection device 100 is powered by a rechargeable battery disposed therein, the power source may charge the rechargeable battery of the muscle power detection device 100 through the interface 106. Further, in some embodiments, the muscle power detection device 100 may be wiredly connected to a remote terminal through the interface 106 and the signal transmission line, such that the processing unit 130 transmits the angle data, the velocity data, the pressure data, the testing time, the muscle power information, the stability information and/or another data or information that can be obtained by the muscle power detection device 100 to the remote terminal.

Figure 4:
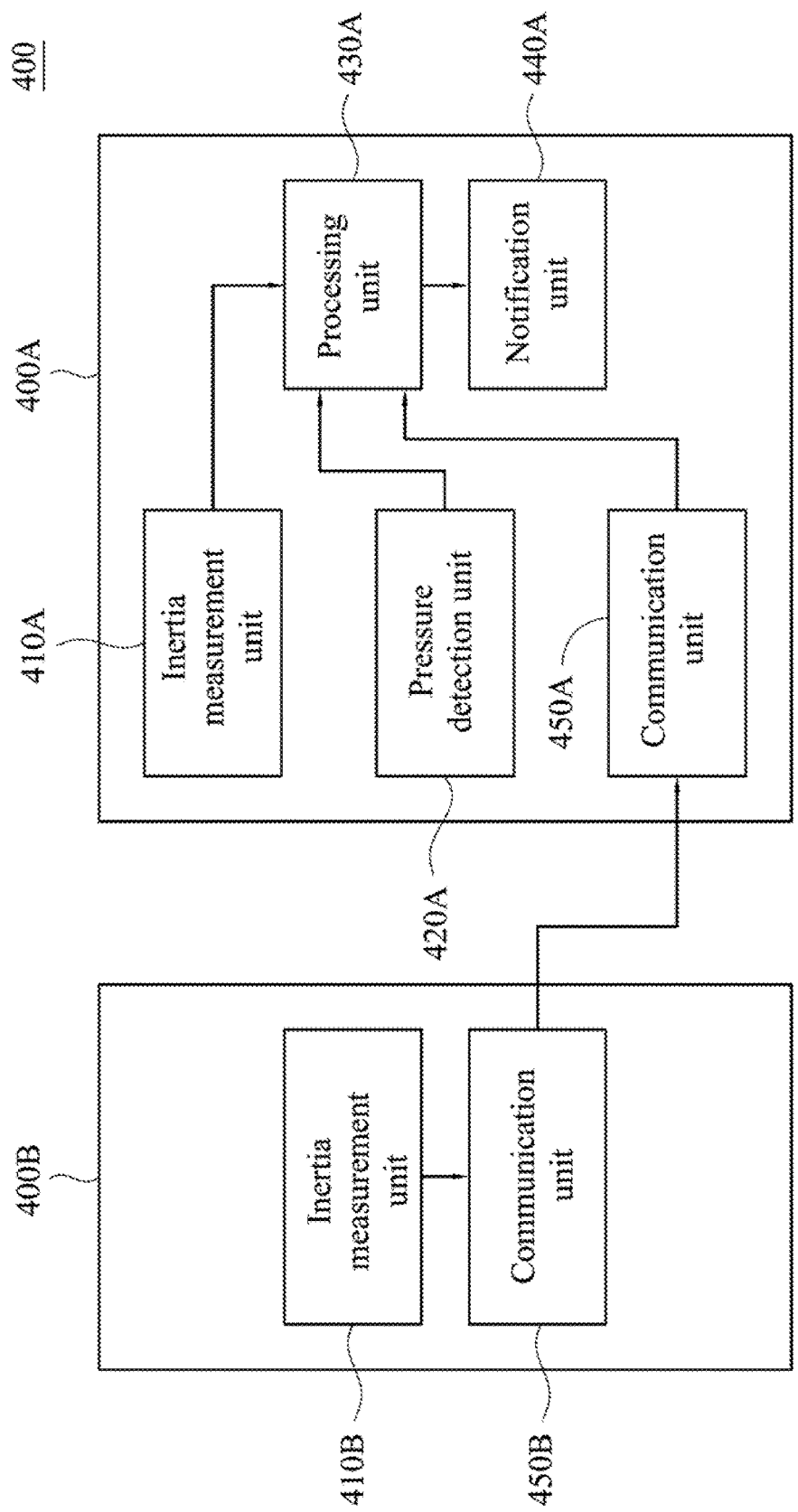
FIG. 4 is a functional block diagram of the muscle power detection device in accordance with some embodiments of the invention.

The muscle power detection device of the invention may also use multiple inertia measurement units which are arranged at the same part or respectively at different parts of a subject. Referring to FIG. 4, FIG. 4 is a functional block diagram of a muscle power detection device 400 in accordance with some embodiments of the invention. As shown in FIG. 4, the muscle power detection device 400 includes a first module 400A and a second module 400B, in which the first module 400A include an inertia measurement unit 410A, a pressure detection unit 420A, a processing unit 430A, a notification unit 440A and a communication unit 450A, and the second module 400B includes an inertia measurement unit 410B and a communication unit 450B. The exterior design of the first module 400A and/or the second module 400B may be the same as the muscle power detection device 100. The first module 400A and the second module 400B may be arranged at the same part or different parts of the subject (e.g. a portion near the elbow joint, the knee joint, the wrist joint or the ankle joint) by a retaining ring, a zip, a hook and loop fastening structure, an elastic band or another component, but is not limited thereto. In the muscle power detection device 400, the inertia measurement units 410A and 410B are approximately the same as or similar to the inertia measurement unit 110 of the muscle power detection device 100, the pressure detection unit 420A is approximately the same as or similar to the pressure detection unit 120 of the muscle power detection device 100, and the notification unit 440A is approximately the same as or similar to the notification unit 140 of the muscle power detection device 100, and therefore the detailed descriptions thereof are not repeated herein.

The communication unit 450B is configured to transmit the inertial data corresponding to the first part obtained by the inertia measurement unit 410A to the communication unit 450A. The communication units 450A and 450B may be connected through a wired communication such as a USB connection and a twisted pair connection or through a wireless communication such as a Bluetooth connection and a WiFi direct connection, but is not limited thereto.

The processing unit 430A is configured to perform a sampling and an operation on the inertial data obtained by the inertia measurement units 410A and 410B in a predetermined testing time, so as to obtain muscle power information corresponding to the first part and the second part. For example, the processing unit 430A performs an operation on the angular velocity data and the acceleration data of the inertia measurement units 410A and 410B to obtain angle data and velocity data of the inertia measurement units 410A and 410B, and then obtains muscle power information corresponding to the first part and the second part according to the angle data and the velocity data of the inertia measurement units 410A and 410B. The testing time of the muscle power detection device 400 and the sampling rate of the processing unit 430A to the inertial data may be adjusted in accordance with, for example, the muscle characteristics and the age of the subject.

In some embodiments, the processing unit 430A may further be configured to perform an operation on the pressure data obtained by the pressure detection unit 420A and to obtain the muscle power information according to the pressure data of the pressure detection unit 420A and the angle data and the velocity data of the inertia measurement units 410A and 410B. In addition, the processing unit 430A may also convert the pressure data, the angle data and the velocity data into an MRC muscle power grade according to the MRC muscle scale.

The muscle power detection device 400 may further include a display unit (not shown) which is configured to real-time display the testing time, the pressure data of the pressure detection unit 420A and/or the muscle power information (such as the MRC muscle power grade) and/or the stability information obtained through the operation of the processing unit 430A, but is not limited thereto. The display unit (not shown) of the muscle power detection device 400 may be arranged in the first module 400A or the second module 400B or structurally independent from the first module 400A and the second module 400B.

Figure 5:
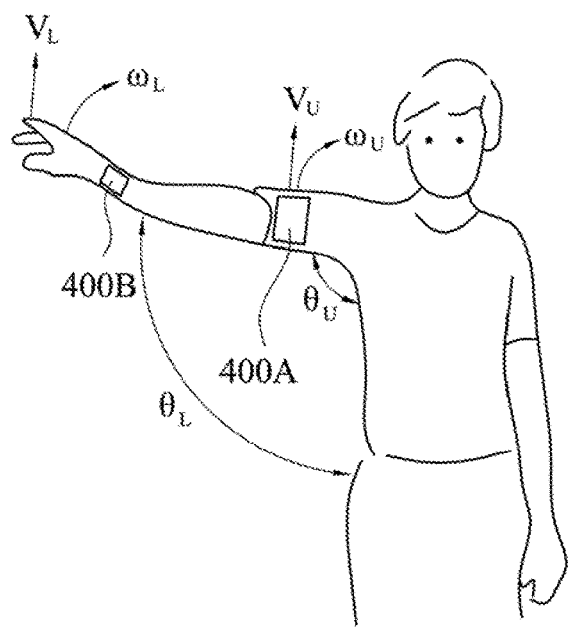
FIG. 5 exemplarily illustrates the muscle power detection device in accordance with some embodiments of the invention arranged on a subject to perform muscle power detection.

FIG. 5 exemplarily illustrates the muscle power detection device 400 arranged on a subject to perform muscle power detection. As shown in FIG. 5, the first module 400A and the second module 400B of the muscle power detection device 400 are arranged respectively at the right arm and the right forearm of the subject, in which an angular velocity ω and an acceleration a are obtained by the inertia measurement units 410A and 410B, respectively, and then angles $\theta_U$ and $\theta_L$ and velocities $V_U$ and $V_L$ are obtained by the processing unit 430A, so as to obtain the muscle power information of the right arm and the right forearm. If the operation result indicates that the angles $\theta_U$ and $\theta_L$ are both less than an angular threshold (the angular threshold may be set between 0 and 5 degrees) and the velocities $V_U$ and $V_L$ are both close to 0, the processing unit 430A determines that there is no muscle contraction at the testing part; that is, the obtained MRC muscle power grade is 0. If the operation result indicates that the angles $\theta_U$ and $\theta_L$ are both greater than the angular threshold and both less than about 90 degrees, the processing unit 430A determines that there is only slight muscle contraction but no joint movement at the testing part; that is, the obtained MRC muscle power grade is 1. If the operation result indicates that the angles $\theta_U$ and $\theta_L$ are both about but do not substantially exceed 90 degrees, the processing unit 430A determines that the testing part can move in a horizontal plane but cannot move against the resistance of gravity; that is, the obtained MRC muscle power grade is 2. If the operation result indicates that the angles $\theta_U$ and $\theta_L$ substantially exceeds 90 degrees, an external force is further needed to be applied on the testing part, in order to further determine the obtained MRC muscle power grade from 3-5.

Figure 6:
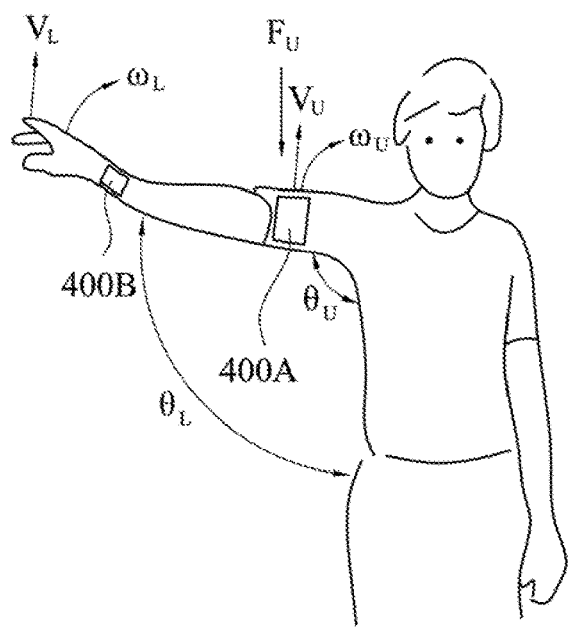
FIG. 6 exemplarily illustrates the muscle power detection device in accordance with some embodiments of the invention arranged on a subject to perform muscle power detection and to apply an external force on a module of the muscle power detection device.

Next, referring to FIG. 6, when applying an external force Fu on the first module 400A, if the operation result indicates that the velocities $V_U$ and $V_L$ are respectively greater than a first velocity threshold and a second velocity threshold and variation quantities of the angles $\theta_U$ and $\theta_L$ are respectively greater than a first angular variation threshold and a second angular variation threshold (the first velocity threshold, the second velocity threshold, the first angular variation threshold and the second angular variation threshold are all greater than 0), the processing unit 430A determines that the testing part can move against the resistance of gravity but cannot move against an external force; that is, the obtained MRC muscle power grade is 3. If the operation result indicates that the velocity $V_U$ is between 0 and the first velocity threshold, the velocity $V_L$ is between 0 and the second velocity threshold, the variation quantity of the angle $\theta_U$ is between 0 and the first angular variation threshold and the variation quantity of the angle $\theta_L$ is between 0 and the second angular variation threshold, the processing unit 430A determines that the testing part can move against the resistance of gravity and a part of external force; that is, the obtained MRC muscle power grade is 4. If the operation result indicates that the velocities $V_U$ and $V_L$ are both substantially 0 and the variation quantities of the angles $\theta_U$ and $\theta_L$ are both substantially 0, the processing unit 430A determines that the testing part can move normally; that is, the obtained MRC muscle power grade is 5. The external force Fu applied on the first module 400A may be displayed by a display unit (not shown) of the muscle power detection device 400, in order to indicate the user whether the external force Fu applied on the first module 400A is suitable. Similarly, the first velocity threshold, the second velocity threshold, the first angular variation threshold and the second angular variation threshold may also be adjusted in accordance with, for example, the muscle characteristics and the age of the subject.

Furthermore, the processing unit 430A may further obtain the stability of the right arm according to the degree of variations of the angles $\theta_L$ and $\theta_U$ and the velocities $V_L$ and $V_U$. For example, if the variation quantities of the angles $\theta_L$ and $\theta_U$ and the velocities $V_L$ and $V_U$ are too large or the variation counts thereof are too high, the processing unit 430A determines that the stability of the muscles of the right arm is insufficient; if the variation quantities and the variation counts of the angles $\theta_L$ and $\theta_U$ and the velocities $V_L$ and $V_U$ are in satisfied ranges (the satisfied ranges may be adjusted in accordance with practical operations), the processing unit 430A determines that the muscles of the right arm have good stability.

In some embodiments, if the first module 400A and the second module 400B are arranged at two sides of a limb joint of a subject, respectively, the processing unit 430A may further determine the bending angle of a joint and/or the correctness of the movement of the subject according to the inertial data obtained by the inertia measurement units 410A and 410B. Taking FIG. 5 as an example, if the difference between the angles $\theta_L$ and $\theta_U$ is too large, or if the variation quantity of the velocity $V_L$ is not positively proportional to that of the velocity $V_U$, the processing unit 430A determines that the right arm of the subject is not in a straight status; that is, the right elbow joint of the subject is determined to have a bend.

Figure 7:
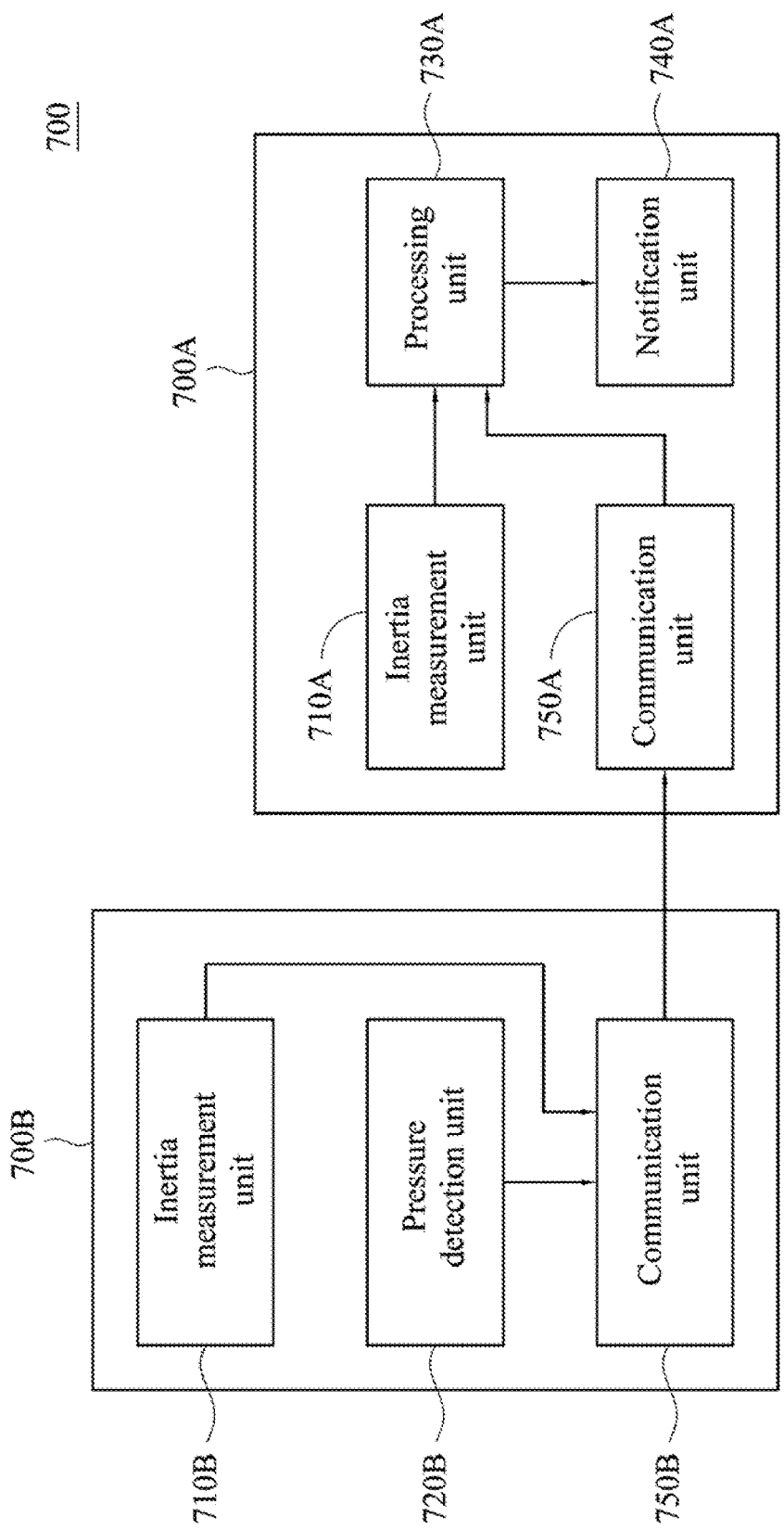
FIG. 7 is a functional diagram of the muscle power detection device in accordance with some embodiments of the invention.
Figure 8:
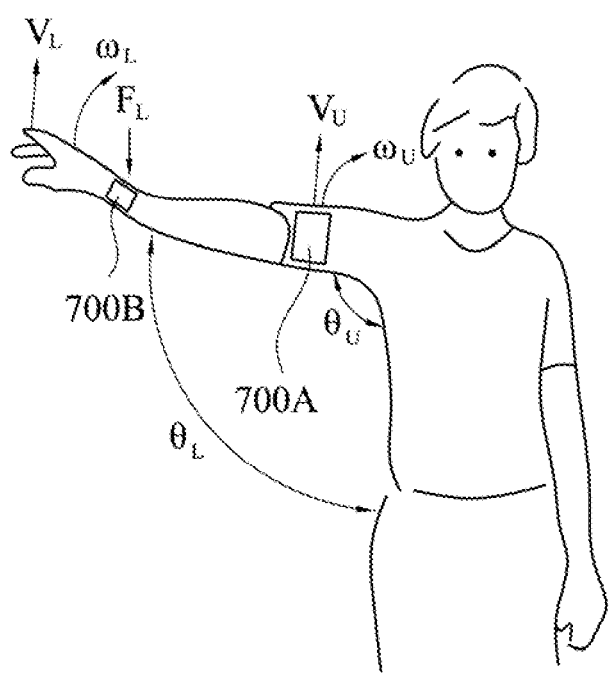
FIG. 8 exemplarily illustrates the muscle power detection device in accordance with some embodiments of the invention arranged on a subject to perform muscle power detection and to apply an external force on a module of the muscle power detection device.

In some other embodiments, the pressure detection unit and the processing unit of the invention may be alternatively arranged in different modules. As shown in FIG. 7, different from FIG. 4, a pressure detection unit 720B is arranged in a second module 700B of a muscle power detection device 700, and a processing unit 730A is arranged in a first module 700A of the muscle power detection device 700; when in use, the pressure detection unit 720B may be arranged at a forearm of a subject, in order to make an external force more effective. In addition, the other components and the arrangements thereof shown in FIG. 7 are approximately the same as or similar to those shown in FIG. 4, and therefore the related descriptions are not repeated herein. The specific arrangement of the muscle power detection device 700 is shown in FIG. 8, in which the inertia measurement units 710A and 710B are similar to the inertia measurement unit 410A; the pressure detection unit 720B is similar to the pressure detection unit 420A; the processing unit 730A is similar to the processing unit 430A; the notification unit 740A is similar to the notification unit 440A; the communication units 750A and 750B are similar to the communication units 450A and 450B, respectively.

It is noted that the muscle power detection device 100 of FIG. 1A and FIG. 1B, the muscle power detection device 400 of FIG. 4 and the muscle power detection device 700 of FIG. 7 are merely some particularly embodiments of the invention and are not intended to limit the scope of the invention. For example, in some other embodiments, the processing unit 130 and/or the notification unit 140 of FIG. 1B may be located in an entity different from the inertia measurement unit 110.

Figure 9:
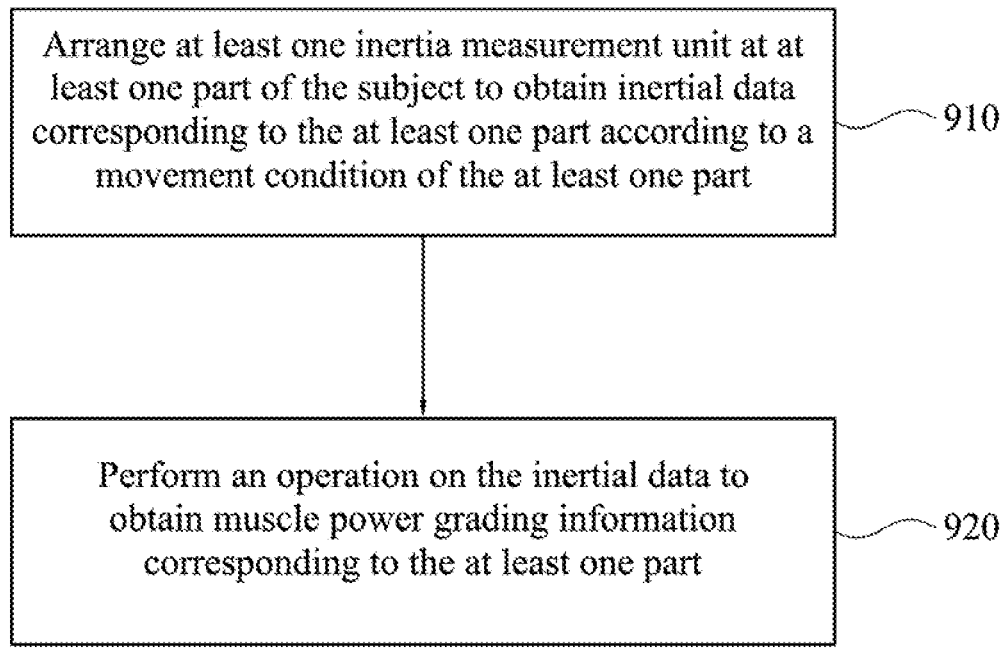
FIG. 9 is a flowchart diagram of a muscle power detection method in accordance with some embodiments of the invention.

Referring to FIG. 9, FIG. 9 is a flowchart diagram of a muscle power detection method 900 in accordance with some embodiments of the invention. The muscle power detection method 900 is configured to detect a muscle power status of a subject and includes the following steps. First, Step 910 is performed, in which at least one inertia measurement unit is arranged at at least one part of the subject, so as to respectively obtain inertial data corresponding to the at least one part of the subject according to a movement status of the at least one part of the subject. The inertia measurement unit may be a nine-axis acceleration sensing module which includes a gyroscope, an accelerometer, an orientation sensor and/or another similar component, and the obtained inertial data thereof include three-axis data such as angular velocity data and acceleration data. Then, Step 920 is performed, in which the inertial data obtained by the at least one inertia measurement unit are operated, so as to obtain muscle power information corresponding to the at least one part. In some embodiments, Step 910 may further include arranging a pressure detection unit on a part of the subject to detect an external force applied on the part. The pressure detection unit and the inertia measurement unit may be arranged at substantially the same part. Step 920 may be correspondingly modified to perform an operation on the inertial data obtained by the inertia measurement unit and the pressure data obtained by the pressure detection unit, so as to obtain the muscle power information corresponding to the at least one part. In particular, the muscle power information obtained through Step 920 may include an MRC muscle power grade which is obtained by performing a conversion according to the MRC muscle scale.

As can be seen from the above description, the muscle power detection device and the muscle power detection method of the invention generates inertial data according to a movement status of a testing part of a subject and generates muscle power information accordingly, so as to facilitate medical staffs such as doctors, physiotherapists and physical therapists to propose corresponding treatments according to the muscle power information and to avoid a risk of misdiagnosis. The muscle power detection device and the muscle power detection method of the invention are non-invasive, which will not result in an uncomfortable experience of a subject. In addition, the muscle power detection device of the invention further includes at least the advantages of small size, portable and low hardware cost.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims.

What is claimed is:

1. A muscle power detection device configured to detect muscle power of a subject, the muscle power detection device comprising:

an inertia measurement unit (IMU) sensor configured to be arranged at a part of the subject and to obtain inertial data corresponding to the part of the subject according to a movement status of the part of the subject;

a pressure detector configured to detect external force applied on the part of the subject to obtain pressure data; and a processor configured to perform an operation on the inertial data and the pressure data for obtaining an evaluation value and to obtain muscle power grading information corresponding to the part of the subject according to the evaluation value, wherein the muscle power grading information comprises Medical Research Council (MRC) muscle power grade information, and wherein the evaluation value includes an angle, a velocity, an angle variation, a velocity variation, or combinations thereof;

wherein if the angle is less than an angular threshold and the velocity is close to 0, then the processor determines that an MRC muscle power grade of the MRC muscle power grade information is 0; if the angle is greater than the angular threshold but less than about 90 degrees, then the processor determines that the MRC muscle power grade is 1; if the angle is about but does not substantially exceed 90 degrees, then the processor determines that the MRC muscle power grade is 2; if the velocity is greater than a velocity threshold and a variation quantity of the angle is greater than an angular variation threshold, then the processor determines that the MRC muscle power grade is 3; if the velocity is between 0 and the velocity threshold and the variation quantity of the angle is between 0 and the angular variation threshold, then the processor determines that the MRC muscle power grade is 4; if the velocity is substantially 0 and the variation quantity of the angle is substantially 0, then the processor determines that the MRC muscle power grade is 5;

wherein the angular threshold is in a range from 0 to 5 degrees, and the velocity threshold and the angular variation threshold are all greater than 0.

2. The muscle power detection device of claim 1, wherein the inertial data of the part of the subject obtained from the IMU sensor comprise angle data and acceleration data, and wherein the angle data and the acceleration data are used to be converted by the processor to the evaluation value.

3. The muscle power detection device of claim 1, wherein the IMU sensor comprises at least one of a gyroscope, an accelerometer and an orientation sensor.

4. The muscle power detection device of claim 1, further comprising a notification unit configured to indicate the muscle power grading information.

5. A muscle power detection device configured to detect muscle power of a subject, the muscle power detection device comprising:

a first inertia measurement unit (IMU) sensor configured to be arranged at a first part of the subject and to obtain first inertial data corresponding to the first part of the subject according to a movement status of the first part of the subject;

a second IMU sensor configured to be arranged at a second part of the subject and to obtain second inertial data corresponding to the second part of the subject according to a movement status of the second part of the subject, wherein the first part of the subject and the second part of the subject are substantially different;

a pressure detector configured to detect external force applied on the first part of the subject or the second part of the subject to obtain pressure data; and a processor configured to perform an operation on the first inertial data, the second inertial data and the pressure data for obtaining an evaluation value and to obtain muscle power grading information corresponding to the first part of the subject and the second part of the subject according to the evaluation value, wherein the muscle power grading information comprises Medical Research Council (MRC) muscle power grade information, and wherein the evaluation value includes an angle, a velocity, an angle variation, a velocity variation, or combinations thereof;

wherein if the angles respectively corresponding to the first part and the second part are all less than an angular threshold and the velocities respectively corresponding to the first part and the second part are all close to 0, then the processor determines that an MRC muscle power grade of the MRC muscle power grade information is 0; if the angles respectively corresponding to the first part and the second part are all greater than the angular threshold but less than about 90 degrees, then the processor determines that the MRC muscle power grade is 1; if the angles respectively corresponding to the first part and the second part are all about but does not substantially exceed 90 degrees, then the processor determines that the MRC muscle power grade is 2; if the velocity corresponding to the first part is greater than a first velocity threshold, the velocity corresponding to the second part is greater than a second velocity threshold, a variation quantity of the angle corresponding to the first part is greater than an first angular variation threshold, and a variation quantity of the angle corresponding to the second part is greater than a second angular variation threshold, then the processor determines that the MRC muscle power grade is 3; if the velocity corresponding to the first part is between 0 and the first velocity threshold, the velocity corresponding to the second part is greater than is between 0 and the second velocity threshold, the variation quantity of the angle corresponding to the first part is between 0 and the first angular variation threshold, and the variation quantity of the angle corresponding to the second part is between 0 and the second angular variation threshold, then the processor determines that the MRC muscle power grade is 4; if the velocities respectively corresponding to the first part and the second part are all substantially 0 and the variation quantities of the angles respectively corresponding to the first part and the second part are all substantially 0, the processor determines that the MRC muscle power grade is 5;

wherein the angular threshold is in a range from 0 to 5 degrees, and the first velocity threshold, the second velocity threshold, the first angular variation threshold and the second angular variation threshold are all greater than 0.

6. The muscle power detection device of claim 5, wherein at least one of the first inertial data of the first part of the subject obtained from the first IMU sensor and the second inertial data of the second part of the subject obtained from the second IMU sensor comprise angle data and acceleration data, and wherein the angle data and the acceleration data are used to be converted by the processor to the evaluation value.

7. A muscle power detection method for detecting muscle power of a subject, the muscle power detection method comprises:

arranging at least one inertia measurement unit (IMU) unit sensor at at least one part of the subject to obtain inertial data corresponding to the at least one part of the subject according to a movement status of the at least one part of the subject;

arranging a pressure detector on one of the at least one part of the subject to detect external force applied on the one of the at least one part of the subject to obtain pressure data; and performing an operation on the inertial data and the pressure data to obtain an evaluation value and to obtain muscle power grading information corresponding to the at least one part of the subject according to the evaluation value, wherein the muscle power grading information comprises Medical Research Council (MRC) muscle power grade information, and wherein the evaluation value includes an angle, a velocity, an angle variation, a velocity variation, or combinations thereof;

wherein if the angle is less than an angular threshold and the velocity is close to 0, then an MRC muscle power grade of the MRC muscle power grade information is determined to be 0; if the angle is greater than the angular threshold but less than about 90 degrees, then the MRC muscle power grade is determined to be 1; if the angle is about but does not substantially exceed 90 degrees, then the MRC muscle power grade is determined to be 2; if the velocity is greater than a velocity threshold and a variation quantity of the angle is greater than an angular variation threshold, then the MRC muscle power grade is determined to be 3; if the velocity is between 0 and the velocity threshold and the variation quantity of the angle is between 0 and the angular variation threshold, then the MRC muscle power grade is determined to be 4; if the velocity is substantially 0 and the variation quantity of the angle is substantially 0, then the MRC muscle power grade is determined to be 5;

wherein the angular threshold is in a range from 0 to 5 degrees, and the velocity threshold and the angular variation threshold are all greater than 0.

* * * * *